United States Patent [19]

Wang et al.

[11] Patent Number: 5,498,787
[45] Date of Patent: Mar. 12, 1996

[54] METHOD FOR PREPARING CEPHALOSPORIN DERIVATIVES

[75] Inventors: Hui-Po Wang; Jia-Shuai Lee, both of Taipei, Taiwan

[73] Assignee: Standard Chemical & Pharmaceutical Co., Ltd., Taiwan

[21] Appl. No.: 230,475

[22] Filed: Apr. 20, 1994

[51] Int. Cl.$^6$ ................................ C07D 501/04
[52] U.S. Cl. .................... 540/222; 540/226; 540/227; 540/225; 540/228
[58] Field of Search ................... 540/226, 222, 540/227, 215, 221, 225

[56] References Cited

PUBLICATIONS

Demuth, T. P. et al., Journal of Antibiotics, 1991, 44(2), 200.
Mobashery et al., Journal of Org. Chemistry, 1986, 51, 4723.

*Primary Examiner*—Nicholas Rizzo
*Attorney, Agent, or Firm*—Fish & Richardson

[57] ABSTRACT

A method for preparing cephalosporin derivatives by reacting cephalosporin alkaline metal salts with organic halide in the presence of quaternary ammonium salts catalyst is disclosed. $\Delta^3 \rightarrow \Delta^2$ isomerization, a side reaction commonly reported in preparation of cephalosporin derivatives was successfully eliminated. The desired $\Delta^3$ was obtained as a sole product in the reaction.

17 Claims, 1 Drawing Sheet

METHOD FOR PREPARING CEPHALOSPORIN DERIVATIVES

BACKGROUND OF THE INVENTION

The present invention relates to the preparation of cephalosporm derivatives.

In the preparation of cephalosporm ester prodrugs, $\Delta^3 \rightarrow \Delta^2$ isomerization was frequently reported to occur in various reaction conditions. The difference between $\Delta^3$ and $\Delta^2$ isomefic compounds are shown as below:

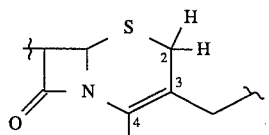

$\Delta^3$: ceph-3-em

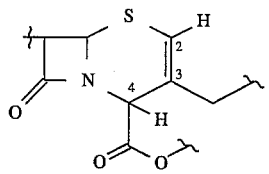

$\Delta^2$: ceph3-em $\Delta^2$ isomers are reactive as antibacterial agents. Due to the structure similarity, these undesired byproducts are very difficult to be separated from the desired $\Delta^3$ isomers. A method of transforming the $\Delta^2$ isomers to $\Delta^3$ isomers is commonly adopted. This method involves two steps of reactions where the $\Delta^2$ isomers are oxidized to their surfoxide derivatives. The surfoxides are then transformed back to the desired $\Delta^3$ isomers upon sodium thionate reduction. However, the two-steps reactions along with relevant isolation and purification processes make this method uneconomical.

T. P. Demuth et al (journal of antibiotics, 1994,44 (2), 200) and S. Mobashery et al ( J. Org. Chem., 1986, 51, 4723) reported methods in preparing cepham esters by using cepham acid, in stead of cepham metal salts, as the starting materials. However, the cepham metal salts has to be transformed to their free acid prior to the reaction and the method in preventing $\Delta^3 \rightarrow \Delta^2$ isomerization is only applicable to certain cepham compounds with a limited solvent system as reaction media. The limitation makes the process not universal and not practical for preparation of cepham esters.

SUMMARY OF THE INVENTION

The principal object of the present invention is to provide a method for preparing cephalosporin ester prodrugs unaccompanied by $\Delta^3 \rightarrow \Delta^2$ isomerization. The present invention provides a method of preparing cephalosporin ester prodrugs of the formula (1)

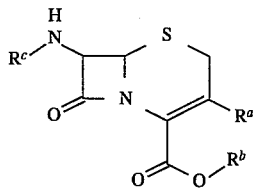

(I)

wherein $R^a$ is $C_{1-4}$ alkyl, $C_{2-5}$ alkoxymethyl, $C_{2-5}$ alkylthiomethyl, $C_{3-6}$ alkylcarboxylmethyl, $-CH_2-O-CO-NH_2$, Ar, $-CH_2$-Ar,-$CH_2-O$-Ar, $-CH_2-S$-Ar or $-CH_2-O-CO-$Ar wherein Ar is a 5 or 6 membered heterocyclic ting containing up to 4 or 5 heteroatoms, respectively, selected from oxygen, sulphur and nitrogen, of which the ting may be substituted by halogen, hydroxy, $C_{1-4}$ alkyl, $C_{1-4}$ alkoxy,$C_{1-4}$ alkylamino or $C_{1-4}$ alkylamido;

$R^b$ $C_{1-4}$ alkyl, $C_{2-4}$ alkenyl, $C_{2-4}$ alkynyl, phenyl, $C_{7-10}$ phenylalkyl, $C_{7-10}$ alkylphenyl, (1-amino) phenyl methyl,

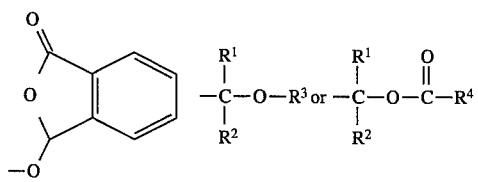

wherein each of $R^1$ and $R^2$ is independently H or $C_{1-4}$ alkyl, $R^3$ is $C_{1-4}$ alkyl, and $R^4$ is $C_{C-4}$ alkyl, $C_{3-6}$ cycloalkyl, $C_{1-4}$ alkoxy, $C_{4-6}$ cycloalkoxy, $C_{1-4}$ alkylamino, $C_{3-6}$ cycloalkylamino,

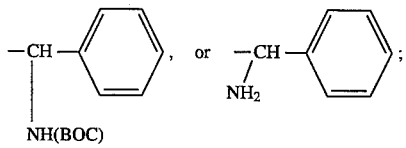

$R^c$ is

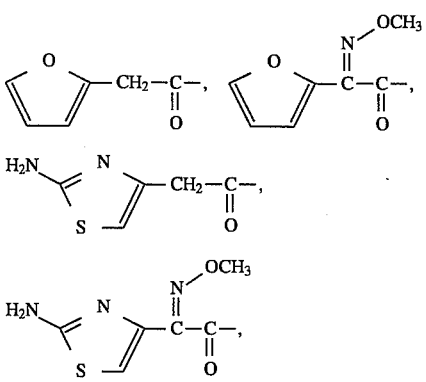

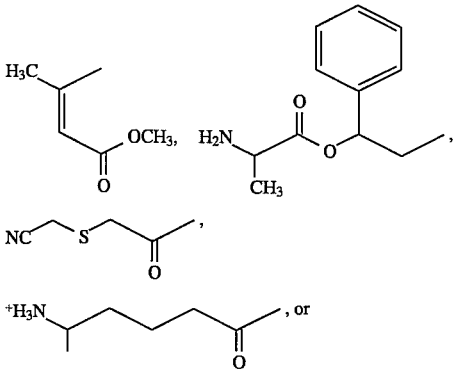

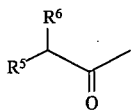

wherein $R^5$ and $R^6$ are the same or different and each is independently hydrogen, $C_{1-4}$ alkyl, hydroxy, phenyl, hydroxy phenyl, amino, thiophene, or tetrazole, and a pharmaceutically acceptable salt thereof, which comprises reacting a compound of the formula (II)

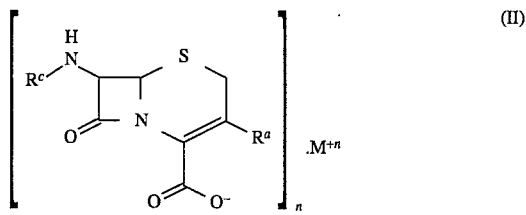

wherein n is 1 or 2, and $M^+n$ is alkaline metal ion when n=1 or alkaline earth metal ion when n=2, and $R^a$ and $R^c$ are as defined above with a compound of the formula (III)

wherein X is halogen, $R^b$ is as defined above, in the presence of a quaternary ammonium or quaternary phosphorium salt catalyst of the formula

wherein Y is nitrogen or phosphorous and Z− is $HSO_4−$ or $H_2PO_4−$ and each of $R^e$, $R^f$, $R^g$ and $R^h$ is independently $C_{1-4}$ alkyl, $C_{3-6}$ cycloalkyl, $C_{6-12}$ aryl, $C_{7-16}$ arylalkyl, or $C_{7-16}$ alkylaryl.

DETAILED DESCRIPTION OF THE PREFERRED EMBODIMENT

The method of the present invention is described below using the example of preparing cefuroxime axetil (as shown in scheme A) and compound D1 (as shown in scheme B)

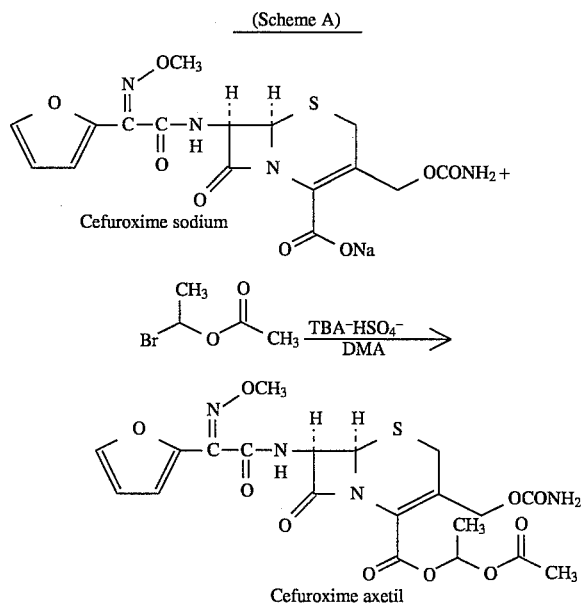

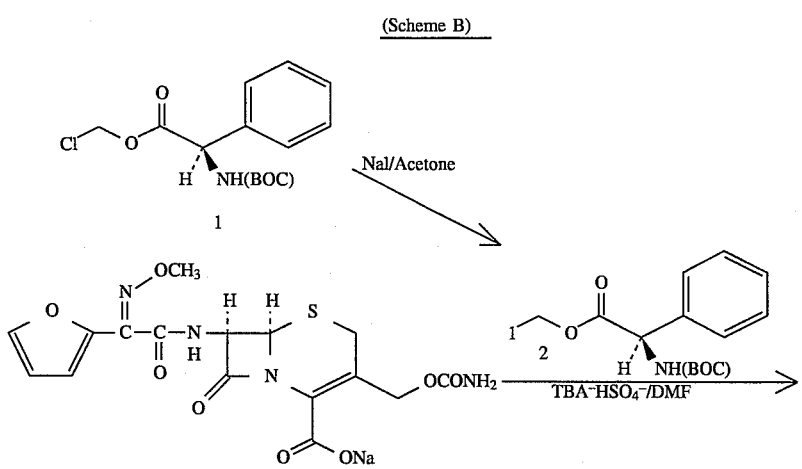

-continued
(Scheme B)

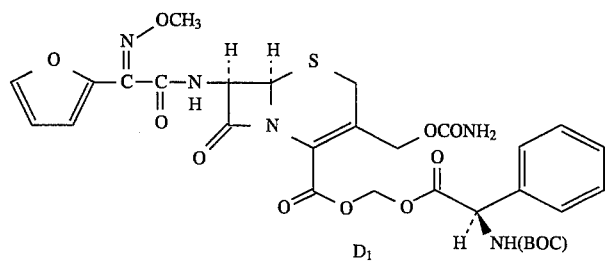

Figure 1:
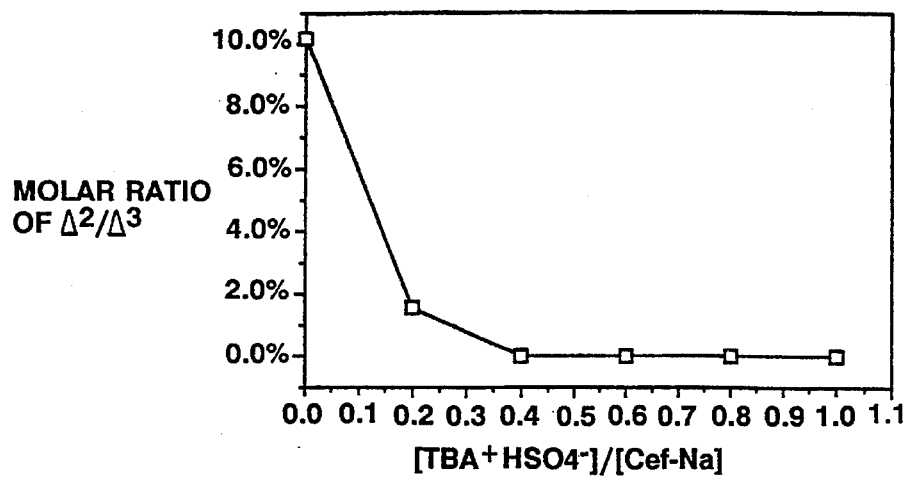
FIG. 1 shows the effect of molar ratio of $(TBA^+HSO_4−)$/cefuroxime sodium on the $\Delta^3 \rightarrow \Delta^2$ isomerization.
Figure 2:
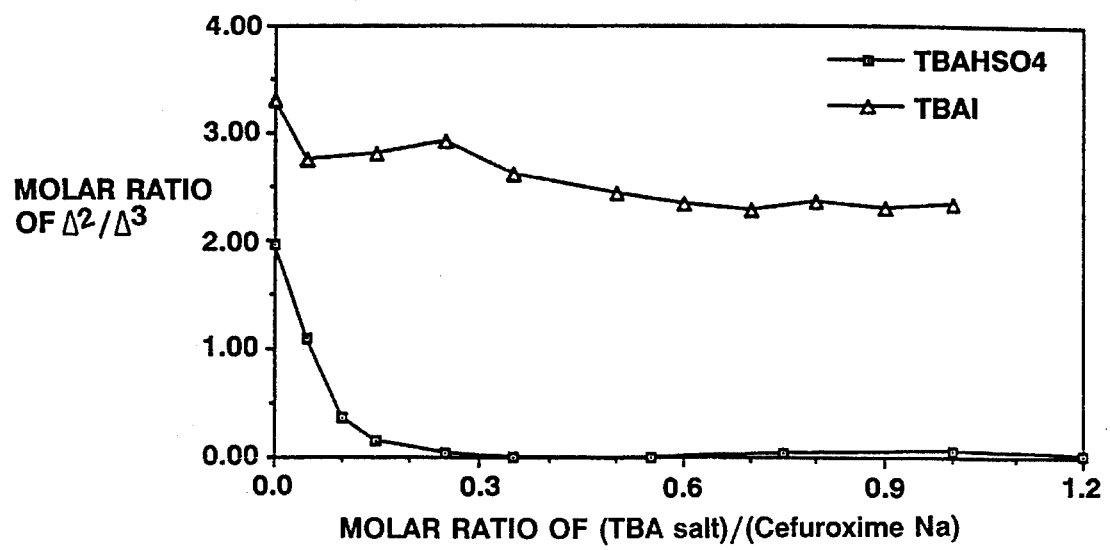
FIG. 2 shows the effect of molar ratio of $(TBA^+HSO_4−)$/cefuroxime sodium and $TBA^+I^−$ cefuroxime sodium on the $\Delta^3 \rightarrow \Delta^2$ isomerization.

The significance of using quaternary ammonium salt with acidic counter ion as catalyst m reaction medium is demonstrated in FIG. 1 and FIG. 2.

Referring to FIG. 1, the drawing shows the effect of $TBA^+HSO_4^-$ on prevention of the alkylation of cefuroxime sodium from undesired $\Delta^3 \to \Delta^2$ isomerization (Scheme A). The axis of abscissa represents molar ratio of $TBA^+HSO_4^-$/cefuroxime sodium used in the reaction and the axis of ordinate denotes the molar ratio of undesired $\Delta 2$ to desired $\Delta 3$ product, obtained from the reaction and monitored by HPLC. As shown in the figure, significant amount of $\Delta^2$ isomer was obtained in reactions where $TBA^+HSO_4^-$ was not added (10% molar ratio of $\Delta^2$ to $\Delta^3$). Isomerization was significantly inhibited if the ratio was beyond 0.2. When the molar ratio of $TBA^+HSO_4^-$ to cefuroxime sodium reached 0.4, the desired $\Delta^3$ was obtained as the sole product. $TBA^+HSO_4^-$ seems to have significant effect in preventing the unfavored $\Delta^3 \to \Delta^2$ isomerization.

FIG. 2 compares the effect of $TBA^+HSO_4^-$ and $TBA^+I^-$ on preventing the reaction (Scheme B) from undesired $\Delta^3 \to \Delta^2$ isomerization. As shown in FIG. 2, more of $\Delta^2$ isomer than the desired $\Delta^3$ isomer was obtained when the molar ratio of $TBA^+HSO_4^-$/ cefuroxime sodium was less than 0.05. Isomerization was significantly inhibited if the ratio was beyond 0.15. When the molar ratio of $TBA^+HSO_4^-$ to cefuroxime sodium reached 0.35, the desired $\Delta^3$ was obtained as the sole product. In reactions catalyzed by $TBA^+I^-$, $\Delta 3 \to \Delta 2$ was obviously favored and the $\Delta^2$ isomer was the major product in all reactions, no matter what the ratio of the catalyst to cefuroxime sodium was.

The present invention clearly demonstrated that the alkylation reaction can be facilitated by the addition of quaternary ammonium salts as catalyst and the $\Delta^3 \to \Delta^2$ isomerization, commonly reported, can be fully eliminated when quaternary ammonium salts with acid counter ion was used as catalyst.

The present invention will be fully understood from the following example 1 and example 2.

Example 1: preparation of cefuroxime axetil (see scheme A above)

Two hundred milligrams of sodium cefuroxime and $TBA^+HSO_4^-$ (30 mg) were added to dimethyl acetamide (1.1 ml) at room temperature. The mixture was stirred and seventy-eight milligrams of 1-acetoxyethylbromide was added. The solution was stirred for 3 hours, aliquot of the solution was withdrawn and analyzed by HPLC (normal phase colmina, $\lambda 277$ nm). No $\Delta^2$ isomer was detected. The product is identical with the authentic cefuroxime axetil.

Another reaction was conducted where the condition was the same as above except that $TBA^+HSO_4^-$ was not added. In this reaction, the $\Delta^2$ isomeric product was detected. The ratio of $[\Delta^2$ isomer$]/[\Delta^3$ isomer$]$ was 10.2%.

Example 2: preparation of cephalosporm ester D 1

(see scheme B above)
1. preparation of iodide intermediate compound 2:

1.5 grams of chloromethyl 2-(BOC) amino-2-phenylacetate (compound 1) and 3.75 grams of sodium iodide were dissolved in 50 ml of acetone. The solution was heated under reflux for 1 hour. Acetone was evaporated. The iodide intermediate (compound 2) was obtained by extracting the residue with 50 ml of methylene chloride. (BOC is an abbreviation of t-bufloxycambonyl).

2. preparation of cephalosporin ester D 1:

The solid residue (compound 2) obtained from the above procedure and 2.24 g (5 m mole) of cefuroxime sodium and 2.04 g (6 m mole) of tetrabutyl ammonium hydrogen sulfate ($TBA^+HSO_4^-$) were dissolved in 50 ml of N.N– dimethyl formamide (DMF). The resulting mixture was stirred under nitrogen atmosphere for 12 hours. DMF was removed in vacuo. The residue was partitioned with ethyl acetate and water. The organic layer was separated, washed with saturated sodium chloride solution, then dried with sodium sulfate. After concentration and purification 2.10 g of a pure cephalosporin ester D 1 was obtained, M.P. 111°–113° C. The product was clearly identified as pure $\Delta^3$ isomer from COSY and 2DNMR. The product was free from the undesired $\Delta^2$ isomer, according to the COSY and 2DNMR data previously analyzed for this isomer.

What is claimed is:

1. A method for preparing a compound of the formula (I)

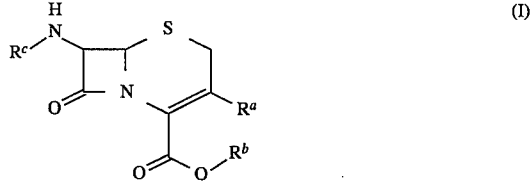

wherein $R^a$ is $C_{1-4}$ alkyl, $C_{2-5}$ alkoxymethyl, $C_{2-5}$ alkylthiomethyl, $C_{3-6}$ alkylcarboxylmethyl, $-CH_2-O-CO-NH_2$, Ar, $-CH_2-Ar$, $-CH_2-O-Ar$, $-CH_2-S-Ar$ or $CH_2-_O-CO-Ar$ wherein Ar is a 5 or 6 membered heterocyclic ring containing up to 4 or 5 heteroatoms, respectively, selected from oxygen, sulphur and nitrogen, of which the ting may be substituted by halogen, hydroxy, $C_{1-4}$ alkyl, $C_{1-4}$ alkoxy, $C_{1-4}$ alkylamino or $C_{1-4}$ alkylamido;

$R^b$ is $C_{1-4}$ alkyl, $C_{2-4}$ alkenyl, $C_{2-4}$ alkynyl, phenyl, $C_{7-10}$ phenylalkyl, $C_{7-10}$ alkylphenyl, (1-amino) phenyl methyl,

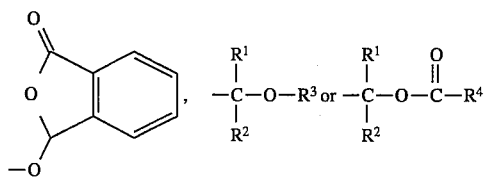

wherein each of $R^1$ and $R^2$ is independently H or $C_{1-4}$ alkyl, $R^3$ is $C_{1-4}$ alkyl, and $R^4$ is $C_{1-4}$ alkyl, $C_{3-6}$ cycloalkyl, $C_{1-4}$ alkoxy, $C_{4-6}$ cycloalkoxy, $C_{1-4}$ alkylamino or $C_{3-6}$ cycloalkylamino,

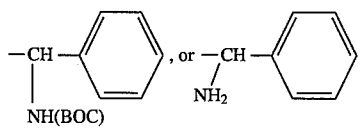

$R^c$ is

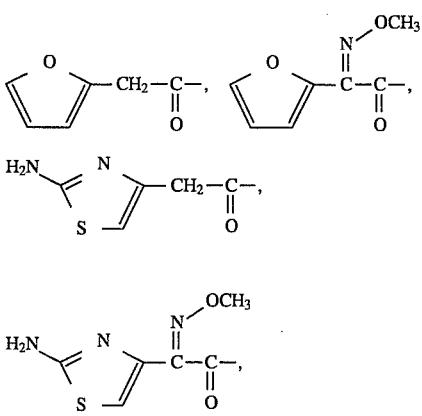

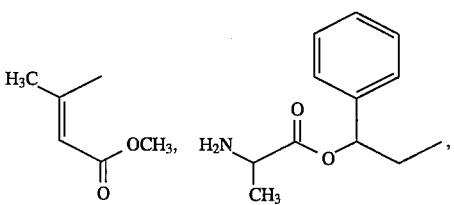

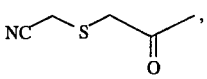

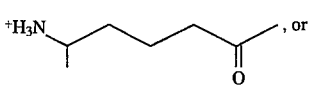

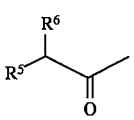

wherein $R^5$ and $R^6$ are the same or different and each is independently hydrogen, $C_{1-4}$ alkyl, hydroxy, phenyl, hydroxy phenyl, amino, thiophene, or tetrazole; and a pharmaceutically acceptable salt thereof; which comprises reacting a compound of the formula (II)

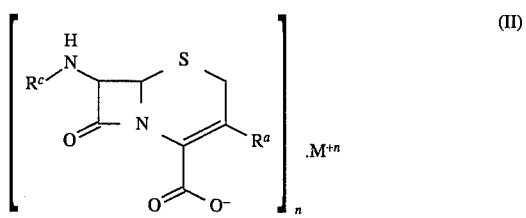

wherein n is 1 or 2, and $M^{+n}$ is alkaline metal ion when n=1 or alkaline earth metal ion when n=2, and $R^a$ and $R^c$ are as defined above with a compound of the formula (III)

$$R^b X \qquad (III)$$

wherein X is halogen, $R^b$ is as defined above, in the presence of a quaternary ammonium or quaternary phosfofium salt catalyst of the formula

wherein Y is nitrogen or phosphorous and Z– is $HSO_4$– or $H_2PO_4$– and each of $R^e$, $R^f$, $R^g$ and $R^h$ is independently $C_{1-4}$ alkyl, $C_{3-6}$ cycloalkyl, $C_{6-12}$ aryl, $C_{7-16}$ arylalkyl, or $C_{7-16}$ alkylaryl.

2. A method as claimed in claim 1 wherein said $R^a$ is —$CH_2$—O—$CH_3$, —$CH_2$—S—$CH_3$, —$CH_2$—O—CO—$CH_3$ or —$CH_2$—O—CO—$NH_2$.

3. A method as claimed in claim 1 wherein said $R^b$ is

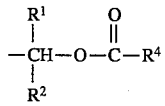

wherein each of $R^1$ and $R^2$ is independently H or $CH_3$, and $R^4$ is $C_{1-4}$ alkyl, $C_{3-6}$ cycloalkyl, $C_{1-4}$ alkoxyl, or $C_{4-6}$ cycloalkoxyl.

4. A method as claimed in claim 1 wherein said $R^c$ is

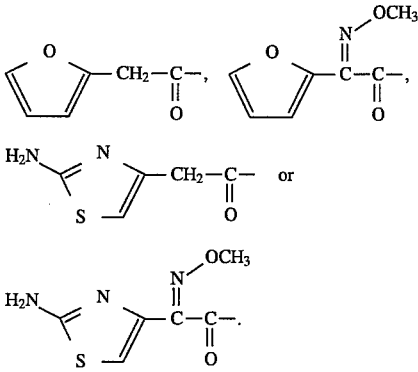

5. A method as claimed in claim 2 wherein said $R^a$ is —$CH_2$—O—$CH_3$.

6. A method as claimed in claim 4 wherein said $R^c$ is

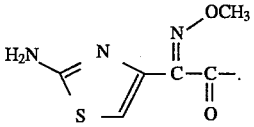

7. A method as claimed in claim 4 wherein said $R^c$ is

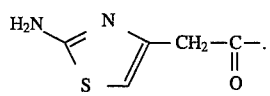

8. A method as claimed in claim 1 wherein said Y is nitrogen and Z– is HSO$_4$–.

9. A method as claimed in claim 1 wherein said quaternary ammonium salt catalyst is tetrabutyl ammonium hydrogen sulfate.

10. A method as claimed in claim 1 wherein said formula (II) is cefuroxime sodium, cefuroxime lithium, cefuroxime potassium or cefuroxime calcium.

11. A method as claimed in claim 1 wherein said formula (I) is

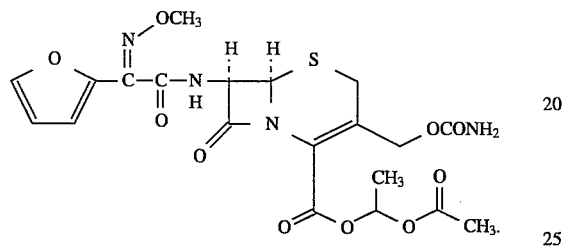

12. A method as claimed in claim 1 wherein said formula (I) is

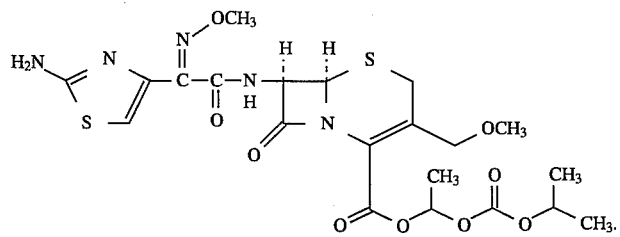

13. A method as claimed in claim 1 wherein said formula (I) is

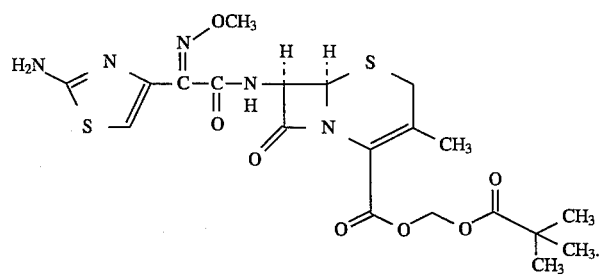

14. A method as claimed in claim 1 wherein said formula (I) is

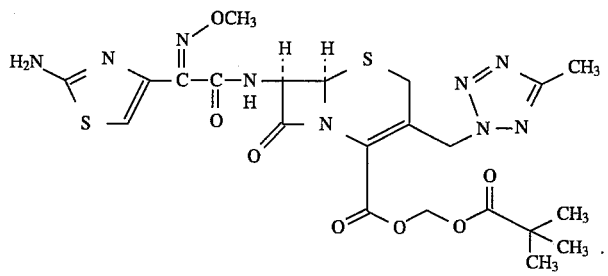
15. A method as claimed in claim 1 wherein said formula (I) is
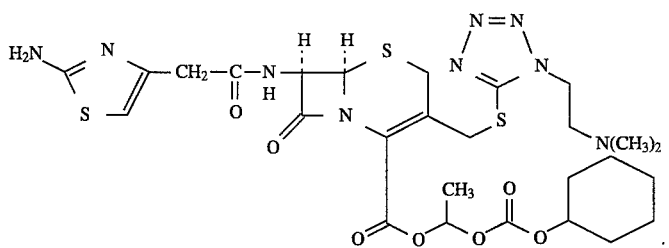
16. A method as claimed in claim 1 wherein said formula (I) is
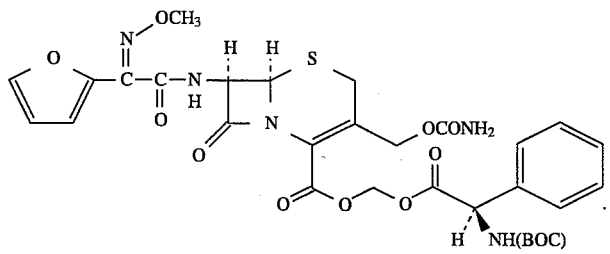
17. A method as claimed in claim 1 wherein said formula (I) is
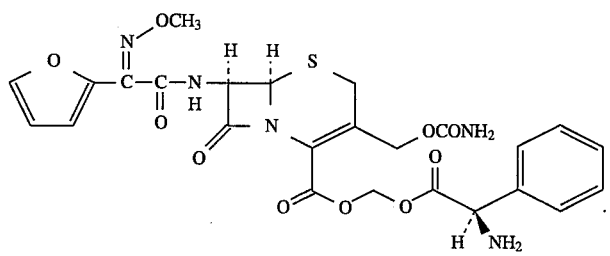
* * * * *